United States Patent [19]
Bisson et al.

[11] Patent Number: 5,622,173
[45] Date of Patent: Apr. 22, 1997

[54] COLOR FLOW DISPLAY WITH COMPENSATION FOR FLOW DIRECTION

[75] Inventors: Janice Bisson, Methuen, Mass.; Lois Scheffler, Derry, N.H.

[73] Assignee: Hewlett-Packard Company, Palo Alto, Calif.

[21] Appl. No.: 576,653

[22] Filed: Dec. 21, 1995

[51] Int. Cl.⁶ ..................................................... A61B 8/00
[52] U.S. Cl. ..................................................... 128/661.01
[58] Field of Search ........................ 128/661.08, 661.09, 128/661.1, 662.01; 73/861.25; 367/104, 105

[56] References Cited

U.S. PATENT DOCUMENTS

| | | | |
|---|---|---|---|
| 4,926,872 | 5/1990 | Brock-Fisher et al. | |
| 5,165,413 | 11/1992 | Maslak et al. | |
| 5,315,999 | 5/1994 | Kinicki et al. | |
| 5,373,848 | 12/1994 | Melton, Jr. et al. | 128/661.09 |
| 5,409,010 | 4/1995 | Beach et al. | 128/661.09 |
| 5,441,052 | 8/1995 | Miyajima | 128/661.09 |

OTHER PUBLICATIONS

IEE Transactions on Biomedical Engineering, vol. BME–30, No. 8, Aug. 1993, Von Ramm et al.—'Beam Steering with Linear Arrays' (pp. 438–452).

*Primary Examiner*—George Manuel

[57] ABSTRACT

An ultrasound imaging system includes a display for displaying an ultrasound image and a transducer for transmitting a linear ultrasound beam which is steerable between positive and negative beam angles about an intermediate azimuth which extends from an emitting face of the transducer. A user input control provides steering signals to cause the transducer to alter the direction angle of transmission of the ultrasound beam. A processor controls the display to produce an image evidencing a first attribute of fluid flowing in a direction towards the transducer and an image with a second attribute of fluid flowing in a direction away from the transducer. The processor is responsive to a steering signal which causes the ultrasound beam to move from one side to the other side of the intermediate azimuth to display the image of fluid flowing in a direction towards the transducer with the second attribute and the image of fluid flowing in a direction away from the transducer with the first attribute. Similarly, the attributes, as displayed by a color bar, are reversed at the same time to be in accordance with the changed blood flow coloration.

6 Claims, 2 Drawing Sheets

COLOR FLOW DISPLAY WITH COMPENSATION FOR FLOW DIRECTION

FIELD OF THE INVENTION

This invention relates to ultrasound flow units and, more particularly, to an ultrasound color flow unit which automatically alters the color mapping of a display in dependence upon changes in the ultrasound beam direction.

BACKGROUND OF THE INVENTION

Ultrasound color flow imaging is a widely used modality to enable the physician to view both venous and arterial blood flows. Many Doppler ultrasound systems employ linear array transducers which comprise a number of small, individual transducer elements arranged, side-by-side, in a single assembly. Two-dimensional images are produced in a sequential linear array scanner. By transmitting an ultrasound signal from each of the array elements (or group of elements) and receiving echo information, for each line of a final display (i.e., a B-mode display), the sequence of image formation results in a rectangular (or parallelogram) image format.

To create an image, a first group of elements is sequentially pulsed, and echoes from the ultrasound waveform are received, and enable derivation of the top B-mode line in the display. At the completion of the transmit/receive operation, a second group of elements is pulsed and the echoes received produce the second line of the display. This sequence continues until the last group of elements has been pulsed to produce the bottom or last line in the display. As a result of electronic scanning of these arrays, very high frame rates are possible which enable real time imaging of flow.

Prior art Doppler systems, which employ linear arrays, have included a user-operated control for altering the direction of transmission of the resultant array of beams. Such control mechanism alters all of the parallel beam paths in a like manner so that a region can be imaged. Prior art Doppler ultrasound systems have also employed a color assignment protocol to enable the user to rapidly identify a direction of arterial or venous flow.

Color map assignment in the prior art systems is based upon whether flow being imaged is away from the transducer array or towards the transducer array. If the transducer's beam path is oriented such that it is imaging flow in a direction away from the transducer (i.e., looking "downstream"), a first color assignment is made. By contrast, if the beam direction of the transducer looks "upstream" so that the flow is in a direction towards the transducer, a second color is assigned. One such color map function is termed "red-away, blue-towards" or RABT. A second color map procedure is "blue-away, red-towards" or BART.

Users of Doppler imaging systems generally prefer to have a single color assignment (e.g. red) to arterial flow and a single color assignment (e.g. blue) to venous flow. However, when a user changes the direction of transmission from a linear array, the ultrasound beam direction changes, for instance, from being directed in the upstream direction, to being directed in the downstream direction. More specifically, if a linear array transducer ultrasound beam is directed to image upstream arterial flow, a subsequent reorientation of the beam can cause it to pass a perpendicular drawn from the surface of the transducer, thus causing the imaging beam to look at downstream flow (with respect to the array). Assuming the ultrasound system is set to utilize a red-away, blue-towards color map, upon beam reorientation, the color of the arterial flow will change from blue to red. As known to those skilled in the art, a Doppler system determines the direction of flow by the sense of the change in the Doppler frequency.

However, it is known that users prefer to have arterial flow imaged in red, whether flowing away or towards the transducer, and venous flow imaged in blue, whether away or towards the transducer. As a result, some Doppler ultrasound systems have a user-operated control which enables reversal of the color map function. Thus, when the user perceives a color change resulting from a beam redirection, user-actuation of the mapping reversal control returns the flow colors to those which were in effect prior to the beam direction change.

Prior art Doppler displays also provide, at one side of the display, a color bar which indicates plural colors assigned to various flow rates, both towards and away from the transducer. Colors assigned to flow which is towards the transducer are often displayed at the top of the color bar and colors assigned to flow which is away from the transducer are displayed at the bottom of the color bar, with the two color areas separated by a "baseline". Such systems also include a control which enables more color intensities to be assigned for imaging of flow velocities in one direction, as compared to flow velocities in the other direction. This action, in effect, causes the baseline to alter its position along the color bar, either upwardly or downwardly, in dependence upon which flow is assigned the greater variety of velocity-representing colors.

When, however, the direction of transmission of the ultrasound beam is moved so that the blood flow being imaged transitions from an away direction to a towards direction, or vice versa, the colors on the top of the color bar switch to representing arterial flow and colors formerly representing venous flow are then on the bottom of the color bar. In addition, the baseline remains unchanged so that if it is off center, the range of colors which display the respective flows are reversed. Only when the user manually reverses the color map function and adjusts the baseline position does the color bar revert to its original color assignments. As a result, when the user perceives flow color changes, the user must be aware of the available means for change of flow color mapping to achieve flow color display continuity. As there are many controls on such ultrasound units, this adds a further level of complexity to the operation of the system.

SUMMARY OF THE INVENTION

An ultrasound imaging system includes a display for displaying an ultrasound image and a transducer for transmitting a linear ultrasound beam which is steerable between positive and negative beam angles about an intermediate azimuth which extends from an emitting face of the transducer. A user input control provides steering signals to cause the transducer to alter the direction angle of transmission of the ultrasound beam. A processor controls the display to produce an image evidencing a first attribute of fluid flowing in a direction towards the transducer and an image with a second attribute of fluid flowing in a direction away from the transducer. The processor is responsive to a steering signal which causes the ultrasound beam to move from one side to the other side of the intermediate azimuth to display the image of fluid flowing in a direction towards the transducer with the second attribute and the image of fluid flowing in a direction away from the transducer with the first attribute. Similarly, the attributes, as displayed by a color bar, are reversed at the same time to be in accordance with the changed blood flow coloration.

DETAILED DESCRIPTION OF A PREFERRED EMBODIMENT

Figure 1:
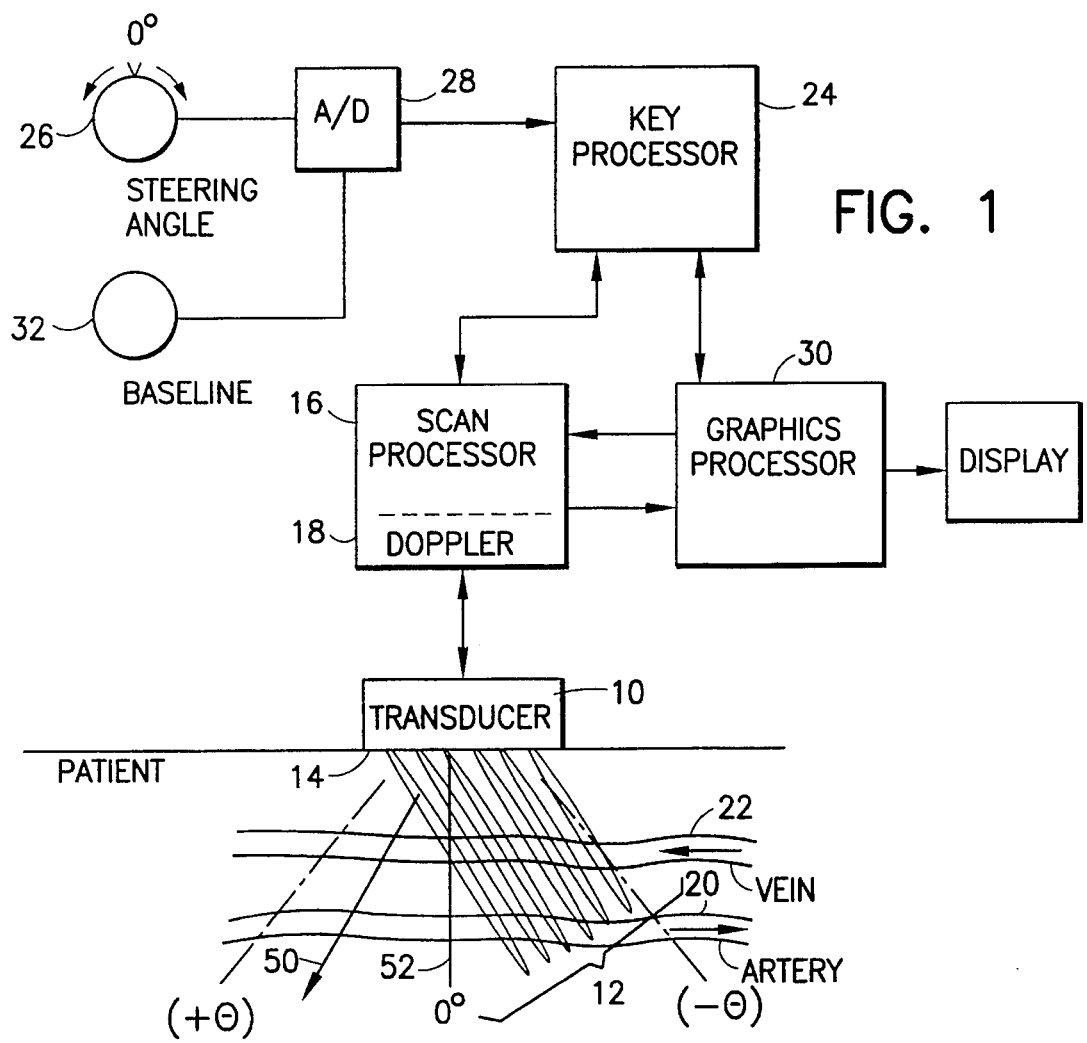
FIG. 1 is a block diagram of an ultrasound system embodying the invention hereof.

FIG. 1 illustrates a high level block diagram of a Doppler ultrasound system. In the embodiment of FIG. 1, a linear array transducer 10 generates a plurality of parallel beams 12 that are changeable in direction azimuth from emitting face 14 in accordance with input control signals. A scan processor 16 includes a Doppler function 18 which enables Doppler flow imaging of blood flow in, for instance, an artery 20 and/or a vein 22.

Scan processor 16, in response to inputs from a key processor 24, causes transducer 10 to reorient the angle of transmission of parallel beams 12 in accordance with a user's alteration of the position of a steering angle knob 26. Movement of steering angle knob 26 causes analog signals to be fed to analog to digital converter 28 which outputs digital values indicative of the analog control inputs. Key processor 24 decodes the steering angle inputs and provides control signals to scan processor 16 which, in turn, determines the amount to move parallel beams 12 in response. Scan processor 16 then provides signals to transducer 10 which causes beams 12 to be skewed to a new directional angle.

Outputs from key processor 24 are also fed to a graphics processor 30 which further receives image data from scan processor 16. Graphics processor 30 includes a procedure which, in conformance with the amount of movement of parallel beams 12, controls the color mapping assigned to arterial/venous flow being imaged by beams 12. Graphics processor 30 further is responsive to inputs from a baseline knob 32 to alter the position of the baseline in a displayed color bar which is indicated on display 34.

Figure 2:
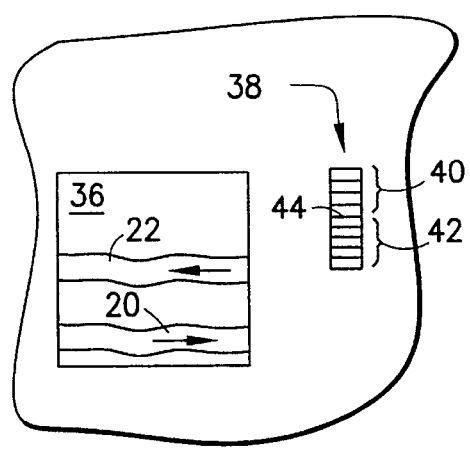
FIG. 2 is an exemplary view of a display of an ultrasound image of a pair of blood vessels, including a color bar.

FIG. 2 illustrates an exemplary display wherein artery 20 and vein 22 are imaged within imaging region 36. A displayed color bar 38 includes an upper portion 40 which represents colors assigned to flow velocities towards transducer 10 and a lower portion 42 for colors assigned to flow velocities away from transducer 10. The colors representing maximum flow velocities towards and away from transducer 10 are positioned at the top and bottom, respectively, of color bar 38 A baseline 44 separates the two color regions of color bar 38. As indicated above, portions 40 and 42 may be adjusted relative to each other so that one portion illustrates more color gradations than the other and thus illustrates a wider range of flow velocities.

So long as ultrasound beams 12 remain oriented in a single direction, all Doppler color mapping remains consistent and no alteration is required. Thus, so long as the ultrasound beams 12 remain oriented as shown in FIG. 1, blood flow in vein 22 remains toward transducer 10 and blood flow in artery 20 remains away from transducer 10. Assuming the user wishes to employ the RABT color map function, arterial flow in artery 20 is colored red and venous flow is colored blue (see FIG. 3a). If, however, beams 12 are reoriented in a clockwise direction so that they point in the direction shown by arrow 50, it can be seen that blood flow in artery 20 is now towards transducer 10 and blood flow in vein 22 is away from transducer 10. In a prior art system (as shown in FIG. 3b), the color mapping (remember it is RABT) would then color red the venous flow in vein 22 and blue the arterial flow in artery 20.

Figure 3A:
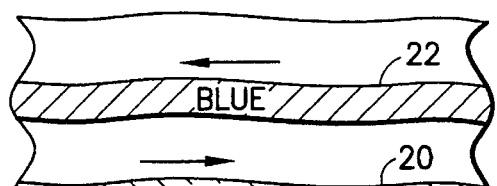
FIG. 3a illustrates a first color mapping resulting from the operation of the system of FIG. 1.
Figure 3B:
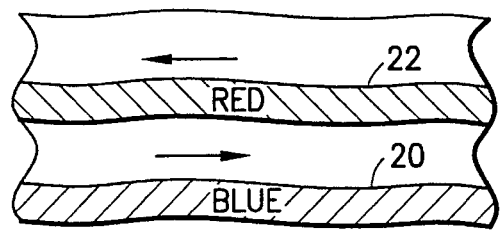
FIG. 3b illustrates a second color mapping resulting from the operation of the system of FIG. 1.
Figure 4:
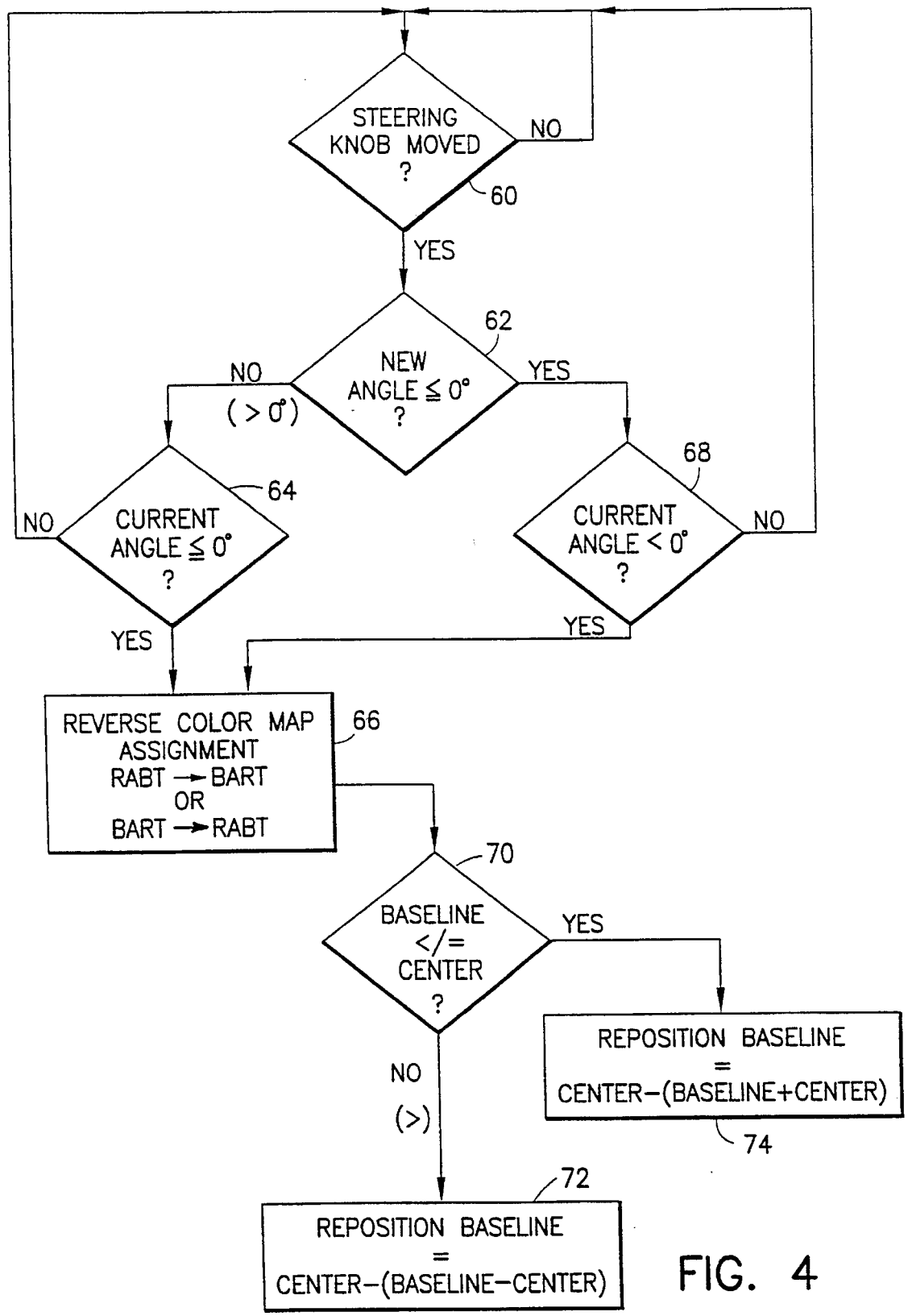
FIG. 4 is a logic flow diagram illustrating the procedure followed by the system of FIG. 1, whereby consistent color mapping is maintained, irrespective of the direction of transmission of the ultrasound beam of FIG. 1.

To avoid this change in color display, graphics processor implements an automatic color map alteration procedure shown in FIG. 4 so that the color mapping display shown in FIG. 3(a) is retained, irrespective of the change in beam transmission direction.

The procedure shown in FIG. 4 is dependent upon graphics processor 30 determining whether the direction of beams 12 are moved past 0° azimuth 52 which extends orthogonally from emitting face 14 of transducer 10. Thus, graphics processor 30 continually monitors the condition of inputs from steering knob 26 (decision box 60). Upon determining that steering knob 26 has been moved, graphics processor 30 next determines whether the new steering angle is less than or greater than the 0° azimuth line (decision box 62).

If it is determined that the new transmission angle is greater than 0°, graphics processor 30 next determines whether the current transmission angle is less than 0°. If the answer is yes (decision box 64), than the steering angle has passed the 0° azimuth and the color map assignment is reversed (box 66). In such manner, graphics processor 30 assures that arterial and venous blood flows continue to be displayed using the previous color assignments, irrespective of the fact that flow directions have changed.

Returning to decision box 64, if it is determined that the current angle is greater than 0°, then there has been no movement of the ultrasound beams past the 0° azimuth and there is no reason to change the color map assignments. The procedure recycles back decision box 60 and awaits the next move of steering knob 26.

Returning to decision box 62, if it is determined that the new angle is less than 0°, graphics processor 30 then determines whether the current angle is greater than 0° (decision box 68). If the answer is yes, the procedure reverses the color map assignment, as shown in box 66. If the answer is no, there has been no movement of the ultrasound beams past the 0° azimuth and the procedure recycles to decision box 60.

Once the color map decision making process is performed, graphics processor 30 determines whether the baseline in color bar 38 should be moved. As previously indicated, the upper portion of color bar 38 is generally assigned to colors representing color assignments to directional flow towards transducer 10 and the bottom portion is assigned colors assigned to directional flow away from transducer 10. Thus, if a color map assignment is reversed, the color mapping (and color gradations) assigned to color bar 38 are also reversed. To determine the repositioning of baseline 44, the procedure first determines (decision box 70) whether baseline 44 is offset from the center of color bar 38. Then, if baseline 44 is at a position above the center of color bar 38 (more colors intensities assigned to away flow), the procedure moves to decision box 72 wherein baseline 44 is re-positioned as determined by the following expression:

flow baseline=center−(flow baseline−center)

where: center is the midpoint of color bar 38.

By contrast, if the flow base line is found to be at a position below the center, then it is repositioned as follows (decision box 74):

flow baseline=center+(center−flow baseline)

In such manner, flow baseline 44 is repositioned automatically and without requirement of user modification.

In summary, the invention enables automatic alteration of color map assignments upon alteration of the beam direction past an intermediate azimuth direction. Thus, the user sees an unchanging color map for both venous and arterial flows, irrespective of the direction of flow with respect to transducer 10.

It should be understood that the foregoing description is only illustrative of the invention. Various alternatives and modifications can be devised by those skilled in the art without departing from the invention. For instance, while Doppler-based ultrasound imaging systems have been described as enabling flow and velocity presentations, other imaging modalities that are capable of measuring flow velocities are also within the scope of the invention. Further, while the transducer array has been described as a planar device, other shapes of transducer arrays are equally usable with the invention so long as they exhibit a steerable beam pattern. Accordingly, the present invention is intended to embrace all such alternatives, modifications and variances which fall within the scope of the appended claims.

We claim:

1. An ultrasound imaging system, comprising:

display means for displaying an ultrasound image;

transducer means for transmitting an ultrasound beam which is steerable between positive and negative transmission angles, about an intermediate azimuth extending orthogonally from an emitting face of said transducer means;

user input means for providing steering signals to cause said transducer means to alter a direction angle of transmission of said ultrasound beam; processor means for controlling said display means to display an image of fluid flowing in a direction towards said transducer means with a first attribute and an image of fluid flowing in a direction away from said transducer means with a second attribute, said processor means responsive to a steering signal which causes said ultrasound beam to be moved from one side of said intermediate azimuth to another side of said intermediate azimuth, to automatically display said image of fluid flowing in a direction towards said transducer means with said second attribute and said image of fluid flowing in a direction away from said transducer means with said first attribute.

2. The ultrasound imaging system as recited in claim 1, wherein said processor means causes said display means to display a color bar having a baseline which separates first plural attributes assigned to fluid flow towards said transducer and second plural attributes assigned to fluid flow away from said transducer, said processor means responsive to a steering signal input which causes said ultrasound beam to be moved from one side of said intermediate azimuth to another side of said intermediate azimuth, to reverse positions of said first plural attributes and second plural attributes on said color bar.

3. The ultrasound imaging system as recited in claim 2, wherein said color bar, at one extremity includes a first color assigned to represent a highest mean fluid velocity towards said transducer means and at a second extremity includes a second color assigned to represent a highest mean fluid velocity away from said transducer means, said color bar including intermediate intensities of said first and second colors between said first color and second colors, respectively, and said baseline.

4. The ultrasound imaging system as recited in claim 1, wherein said first attribute is a first color group and said second attribute is a second color group.

5. A method for ultrasound imaging, comprising the steps of:

displaying an ultrasound image on a display means;

transmitting an ultrasound beam which is steerable between positive and negative transmission angles about an intermediate azimuth extending orthogonally from an emitting face of a transducer means;

providing steering signals to cause said transducer means to alter a transmission angle of said ultrasound beam;

controlling said display means to display an image of fluid flowing in a direction towards said transducer means with a first attribute and an image of fluid flowing in a direction away from said transducer means with a second attribute; and responding to a steering signal which causes said ultrasound beam to be moved from one side of said intermediate azimuth to another side of said intermediate azimuth, to automatically display said image of fluid flowing in a direction towards said transducer means with said second attribute and said image of fluid flowing in a direction away from said transducer means with said first attribute.

6. The method for ultrasound imaging as recited in claim 5, further comprising the steps of:

displaying a color bar on said display means, said color bar having a baseline which separates first displayed plural attributes assigned to fluid flow towards said transducer and second displayed plural attributes assigned to fluid flow away from said transducer;

responding to a steering signal which causes said ultrasound beam to be moved from one side of said intermediate azimuth to another side of said intermediate azimuth, to reverse positions of said first displayed plural attributes and said second displayed plural attributes on said color bar.

* * * * *